(12) United States Patent  (10) Patent No.: US 9,421,544 B2
Wang  (45) Date of Patent: Aug. 23, 2016

(54) THREE-DIMENSIONAL DIGITAL MICROFLUIDIC SYSTEM

(71) Applicant: Gary Chorng-Jyh Wang, Cupertino, CA (US)

(72) Inventor: Gary Chorng-Jyh Wang, Cupertino, CA (US)

( * ) Notice: Subject to any disclaimer, the term of this patent is extended or adjusted under 35 U.S.C. 154(b) by 553 days.

(21) Appl. No.: 13/781,181

(22) Filed: Feb. 28, 2013

(65) Prior Publication Data

US 2013/0220810 A1  Aug. 29, 2013

Related U.S. Application Data

(60) Provisional application No. 61/604,910, filed on Feb. 29, 2012.

(51) Int. Cl.
| | | |
|---|---|---|
| B01L 3/00 | (2006.01) | |
| B01L 1/00 | (2006.01) | |
| B81B 1/00 | (2006.01) | |
| B01F 13/00 | (2006.01) | |

(52) U.S. Cl.
CPC ....... B01L 3/502792 (2013.01); B01F 13/0071 (2013.01); B01F 13/0076 (2013.01); B01L 3/563 (2013.01); B81B 1/00 (2013.01); *B01L 2300/0816* (2013.01); *B01L 2300/0874* (2013.01); *B01L 2400/0427* (2013.01)

(58) Field of Classification Search
CPC .. B01L 3/502792; B81B 1/00; B01F 13/0071
See application file for complete search history.

(56) References Cited

U.S. PATENT DOCUMENTS

| | | | |
|---|---|---|---|
| 919,138 | A | 4/1909 | Drake et al. |
| 3,819,039 | A | 6/1974 | Erickson |
| 4,011,873 | A | 3/1977 | Hoffmeister |
| 5,207,703 | A | 5/1993 | Jain |
| 5,364,410 | A | 11/1994 | Failla et al. |
| 5,397,326 | A | 3/1995 | Mangum |
| 5,562,685 | A | 10/1996 | Mollenauer et al. |
| 5,624,446 | A | 4/1997 | Harryman, II |
| 5,653,719 | A | 8/1997 | Raiken |
| 5,681,333 | A | 10/1997 | Burkhart et al. |
| 5,702,407 | A | 12/1997 | Kaji |
| 5,713,908 | A | 2/1998 | Jameel et al. |
| 5,797,929 | A | 8/1998 | Andreas et al. |
| 6,022,360 | A | 2/2000 | Reimels et al. |
| 6,099,538 | A | 8/2000 | Moses et al. |
| 6,558,399 | B1 | 5/2003 | Isbell et al. |
| 6,723,107 | B1 | 4/2004 | Skiba et al. |
| 6,893,448 | B2 | 5/2005 | O'Quinn et al. |
| 6,969,394 | B2 | 11/2005 | Snyder |
| 7,118,583 | B2 | 10/2006 | O'Quinn et al. |
| 7,364,541 | B2 | 4/2008 | Chu et al. |
| 8,252,159 | B2 | 8/2012 | Roux et al. |

(Continued)

OTHER PUBLICATIONS

Berthier et al. (NSTI-Nanotech 2006, www.nsti.org, ISBN 0-9767985-6-5 vol. 1, 2006).*

(Continued)

*Primary Examiner* — Luan Van
*Assistant Examiner* — Steven Rosenwald
(74) *Attorney, Agent, or Firm* — Haverstock & Owens LLP

(57) ABSTRACT

A three-dimensional digital microfluidic system comprises a first plate with a first electrode, a second plate with a second electrode, and a microfluidic drop in between the first and the second electrode. The electrodes are able to be actuated in sequence such that the microfluidic drop is able to be transported. A bridge plate is able to be included.

22 Claims, 3 Drawing Sheets

(56) References Cited

U.S. PATENT DOCUMENTS

| | | |
|---|---|---|
| 2001/0002436 A1 | 5/2001 | Bowman et al. |
| 2001/0037119 A1 | 11/2001 | Schmieding |
| 2001/0053916 A1 | 12/2001 | Rioux |
| 2002/0147456 A1 | 10/2002 | Diduch et al. |
| 2002/0188304 A1 | 12/2002 | Mollenauer et al. |
| 2003/0055439 A1 | 3/2003 | Koseki |
| 2003/0078599 A1 | 4/2003 | O'Quinn et al. |
| 2003/0083675 A1 | 5/2003 | Marshall et al. |
| 2003/0208208 A1 | 11/2003 | Chu |
| 2004/0055536 A1* | 3/2004 | Kolar et al. ................ 118/626 |
| 2004/0073233 A1 | 4/2004 | Jannot |
| 2004/0176802 A1 | 9/2004 | Skiba et al. |
| 2004/0249393 A1 | 12/2004 | Weisel et al. |
| 2005/0092606 A1 | 5/2005 | Reich |
| 2005/0222589 A1 | 10/2005 | Chu |
| 2006/0069399 A1 | 3/2006 | Weisel et al. |
| 2006/0074438 A1 | 4/2006 | Chan |
| 2007/0118153 A1 | 5/2007 | Funamura et al. |
| 2008/0097482 A1 | 4/2008 | Bain et al. |
| 2009/0005794 A1 | 1/2009 | Lowry |
| 2009/0035644 A1 | 2/2009 | Markoski et al. |
| 2009/0062819 A1 | 3/2009 | Burkhart et al. |
| 2009/0082788 A1 | 3/2009 | ElMaraphy |
| 2010/0170812 A1 | 7/2010 | Odierno |
| 2010/0198235 A1 | 8/2010 | Pierce et al. |
| 2011/0118757 A1 | 5/2011 | Pierce |
| 2011/0152893 A1 | 6/2011 | Vijayanagar |
| 2011/0247934 A1 | 10/2011 | Wang et al. |
| 2012/0209300 A1 | 8/2012 | Torrie |

OTHER PUBLICATIONS

V. Peukov et al., "Electrowetting: A Model for Contact-Angle Saturation", Colloid Polym Sci 278: pp. 780-793, Springer-Verlag 2000.

* cited by examiner

THREE-DIMENSIONAL DIGITAL MICROFLUIDIC SYSTEM

CROSS-REFERENCE TO RELATED APPLICATIONS

This application claims priority from U.S. Provisional Patent Application Ser. No. 61/604,910, filed Feb. 29, 2012 and entitled Three-Dimensional Digital Microfluidic System, which is hereby incorporated herein by reference in its entirety for all purposes.

FIELD OF THE INVENTION

The invention relates to a three-dimensional digital microfluidic system to provide better droplet routing capabilities and to fit more functions in a given area. The invention also relates to the capability to perform the multi-chip system integration. The system is able to be used to construct LOC (Lab-on-Chip) system structure and advanced multi-chip system integration.

BACKGROUND OF THE INVENTION

The typical digital microfluidic system, based on electrowetting-on-dielectric (EWOD), is based on a two-dimensional architecture, including (1) open system where the droplet is sitting freely on the open substrate and (2) covered system where the droplet is confined between two plates.

SUMMARY

In some embodiments, the present invention expands the two-dimensional conventional digital microfluidic architecture into a three-dimensional architecture. The present invention is able to work on the principle that back and forth motions between open and covered regions are viable under electrowetting actuation.

In some embodiments, two face-to-face plates form the base structure of the two-layer microfluidic operations and a dual open/covered hybrid design adds the inter-layer microfluidic connection to complete the three-dimensional system.

In some embodiments, the present invention constructs a three-dimensional architecture combining both open and covered configuration of the two-dimensional system to provide better routing capability in one system and to provide the ability to bridge multiple microfluidic systems together.

In some embodiments, the three-dimensional digital microfluidic system is constructed by two face-to-face plates. Two of the examples of the three-dimensional microfluidic systems are disclosed here.

The first system comprises the Dual-Layer System that enables microfluidic operations on dual layers. This provides better capabilities to route droplets to blocked locations or to avoid unwanted path contaminations.

The second system is the Inter-Chip Bridge that enables the inter-chip droplet transport capabilities. LOC system is able to be partitioned into smaller self-contained modules and connected by the Inter-Chip Bridge. Moreover, components with incompatible manufacturing are able to be combined in a single LOC system for heterogeneous integration.

In a first aspect, a three-dimensional digital microfluidic system comprising a first plate with a first electrode, a second plate with a second electrode, and a microfluidic droplet in between the first and the second electrode. In some embodiments, the first plate is parallel to the second plate. In other embodiments, the first plate is non-parallel to the second plate. In some other embodiments, the first electrode is facing the second electrode. In some embodiments, the system further comprises a gap between the first plate and the second plate. In some other embodiments, the gap is in the range of 1 µm to 10 cm. In some embodiments, the system further comprises a first gap at a first side larger than a second gap of the second side of the first plate and the second plate.

In some embodiments, each of the first electrode and the second electrode comprises at least one droplet actuating electrode. In other embodiments, the microfluidic droplet is manipulated by actuating in sequence of the electrodes on either or both plates. In other embodiments, the microfluidic droplet is in physical contact with either one of the first plate and the second plate. In some other embodiments, the microfluidic droplet is in physical contact with both of the first and the second plate. In some embodiments, the microfluidic droplet is actuated by the electrodes on the first plate, the second plate, or a combination thereof. In other embodiments, the system further comprises an electrowetting actuation mechanism to control a motion of the microfluidic droplet. In some other embodiments, each of the first plate comprises a first body and the second plate comprises a second body facing each other, wherein a first gap at one end between the first and the second plate is larger than a second gap at the opposite end between the first and the second plate. In some other embodiments, the system further comprises a controlling unit controlling a movement of the microfluidic droplet, such the microfluidic droplet is able to be moved to be in a physical contact with either one of the first plat or the second plate or both.

In a second aspect, a three-dimensional digital microfluidic system comprising a first plate with a first electrode, a second plate with a second electrode, and a bridge plate with a third electrode facing the first and the second electrodes, wherein the bridge plate comprises at least a first portion overlapping with the first plate and at least a second portion overlapping with the second plate. In some embodiments, the system further comprises a microfluidic fluid droplet. In some other embodiments, the microfluidic fluid droplet is sandwiched between the first plate and the bridge plate. In some embodiments, the microfluidic fluid droplet is sandwiched between the second plate and the bridge plate. In other embodiments, the microfluidic fluid droplet is only in physical contact with the bridge plate. In some other embodiments, the system further comprises a first gap between the first plate and the bridge plate and a second gap between the bridge plate and the second plate. In some embodiments, the first gap is equal in size to the size of the second gap. In other embodiments, the first gap is larger than the second gap.

In a third aspect, a method of using a three-dimensional digital microfluidic system comprising moving a microfluidic droplet between a first plate and a second plate by actuating at least one of electrodes on the first, the second plate, or both, wherein the electrodes on the first plate and the second plate are facing each other. In some embodiments, the method further comprises moving the microfluidic droplet from a sandwiched configuration having physical contacts with both of the first and the second plate to a single contact configuration having physical contact with one of the first or the second plate. In other embodiments, the method further comprises moving the microfluidic droplet from a single contact configuration having physical contact with one of the first or the second plate to a sandwiched configuration having physical contacts with both of the first and the second plate. In some embodiments, the first and the second plate are non parallel to each other. In other embodiments, In a fourth aspect, a method of using a three-dimensional digital microfluidic system comprising moving a microfluidic droplet from a first plate to a second plate via a bridge plate, wherein the first, the second, and the bridge plate comprise a first electrode, a second electrode, and a bridge electrode. In some embodiments, the method further comprises actuating the first, the bridge, and the second electrode in sequence such that the microfluidic droplet is transported from the first plate to the third plate. In other embodiments, the first and the second electrodes are facing the bridge electrode.

DETAILED DESCRIPTION

Figure 1:
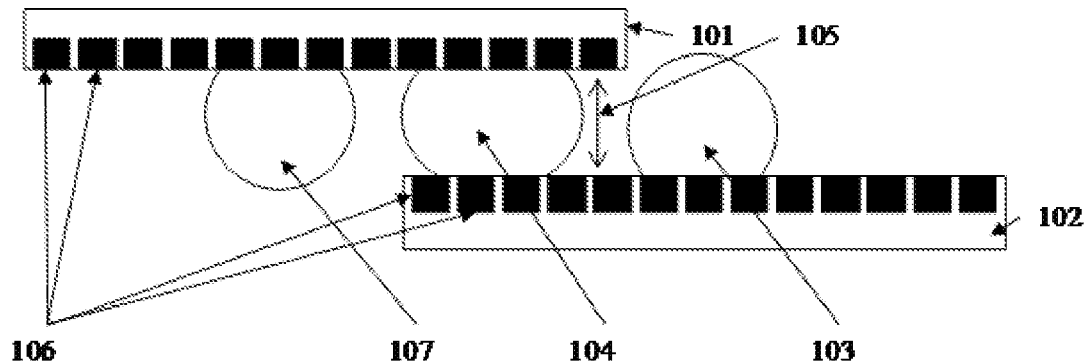
FIG. 1 is a diagram illustrating a basic three dimensional digital microfluidic system in accordance with some embodiments of the present invention.

In some embodiments, the present invention, a three-dimensional digital microfluidic system, based on EWOD, comprising two face-to-face plates separated by a gap in between. Droplets are able to be manipulated by a sequence of actuation of the electrodes on the plates to perform the desired functions. FIG. 1 illustrated a three-dimensional digital microfluidic system in accordance with some embodiments of the present invention. The plate 101 and plate 102 are separated with the gap distance 105. The electrodes 106 on both plate 101 and 102 face each other. Each of the square boxes of the electrodes 106 is able to be independently controlled. In other words, each of the square boxes is able to be an independently controlled electrode. In some embodiments, the multiple electrodes 106 on the plate 101 are controlled in sequence, such that a microfluidic droplet is able to be moved in a pre-determined direction, distance, and/or speed by actuating the multiple electrodes 106 on the plate 101. Similar functional principles also apply to plate 102 and the plates throughout the present specification.

In the three-dimensional digital microfluidic system, an open configuration comprises a droplet 103 sitting on a plate 102 without touching the other plate 101. In this configuration, the droplet 103 is actuated by the electrodes on the plate 102. Similarly, droplet 107 is also at an open configuration and is actuated by plate 101. A covered configuration is a droplet 104 sandwiched between the plate 101 and plate 102 and the droplet 104 can be actuated by the electrodes on plate 101 and/or plate 102.

Figure 2:
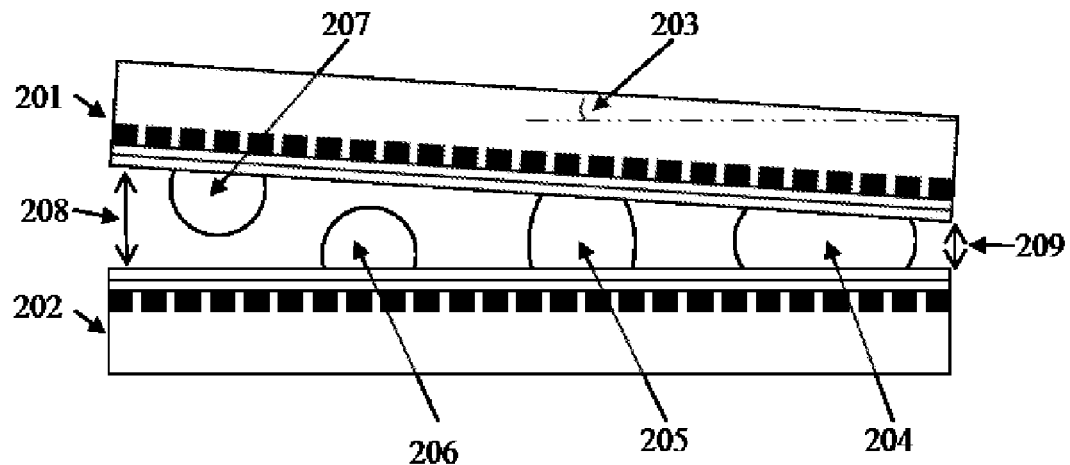
FIG. 2 is a diagram illustrating a Dual-Layer System in accordance with some embodiments of the present invention.

FIG. 2 illustrates a Dual-Layer System. A Dual-Layer System is constructed with two plates, plate 201 and plate 202, and the two plates face each other in an angle 203. Because of the construction with an angle, the gap distance between plate 201 and plate 22 is smaller on one side and bigger on the opposite side and this structure creates a dual open and covered configuration. Droplets in locations 204 and 205 are in covered configuration sandwiched between plate 201 and plate 202 near the smaller gap distance 209. Droplets in locations 206 and 207 are in an open configuration.

In some embodiments, the present invention works on the principle that back and forth motions between open and covered regions are viable under electrowetting actuation. Microfluidic operations of the dual-layer system leverage the best of a dual open/covered hybrid design that droplet transporting and mixing are performed on the open region of the stacked dual-layer system and droplet creation and splitting are performed at the covered region.

As illustrated in FIG. 2, droplet 205 is created from reservoir 204 under covered configuration. At the covered region, the flexibility of switching microfluidic actuations between the top and bottom plates is needed. While the droplet actuation is on the top plate 201 then the bottom plate 202 is configured into a zero potential plate and vice versa. A top-plate actuation of droplet 205 to the left eventually result in a sessile droplet 207 breaking up from the bottom plate when the gap is wide enough. Similarly, a bottom-plate actuation results in a sessile droplet 206 on the bottom plate. A coplanar actuation of the sessile droplet is then provided to move the sessile droplet around.

The tilted angle 203 is able to be one dimensional that gap differences are only along one axis (x- or y-axis) or two dimensional that both x-axis and y-axis have different gaps.

Figure 3:
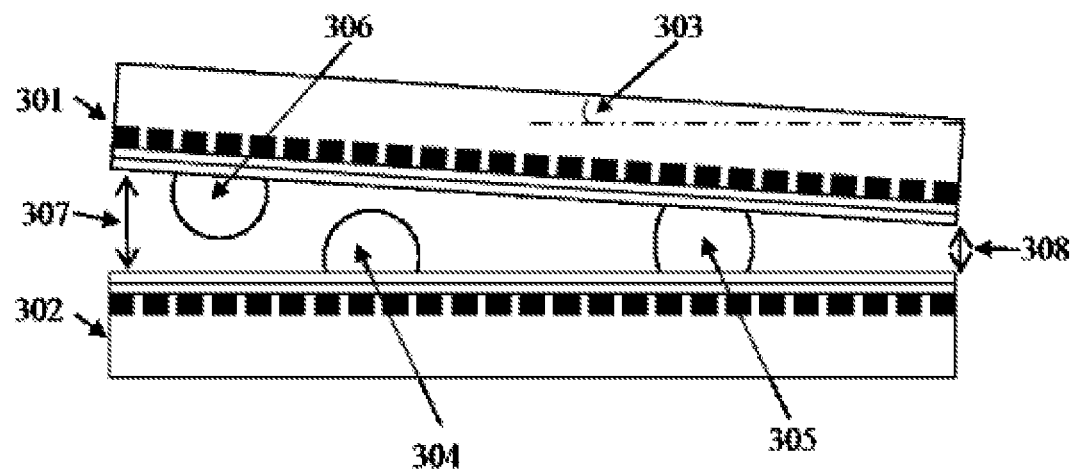
FIG. 3 is a diagram illustrating a droplet in the Dual-Layer System moving from the one plate to the other plate in accordance with some embodiments of the present invention.

FIG. 3 illustrates a droplet switches plates through the inter-layer connection in a Dual-Layer System. A Dual-Layer System is constructed with two plates, plate 301 and plate 302, and the two plates face each other in an angle 303. A drop is originally in an open configuration close to bigger gap distance 307. The gap 308 comprises a smaller gap than the gap 307. By actuating the electrodes on plate 302 in the direction from location 304 to location 305, the droplet in location 304 moves to the right and stops at location 305 in a covered configuration. Then by actuating the electrodes on plate 301 in the direction from location 305 to 306, the droplet in location 305 switches to plate 301 and stops at location 306.

Figure 4:
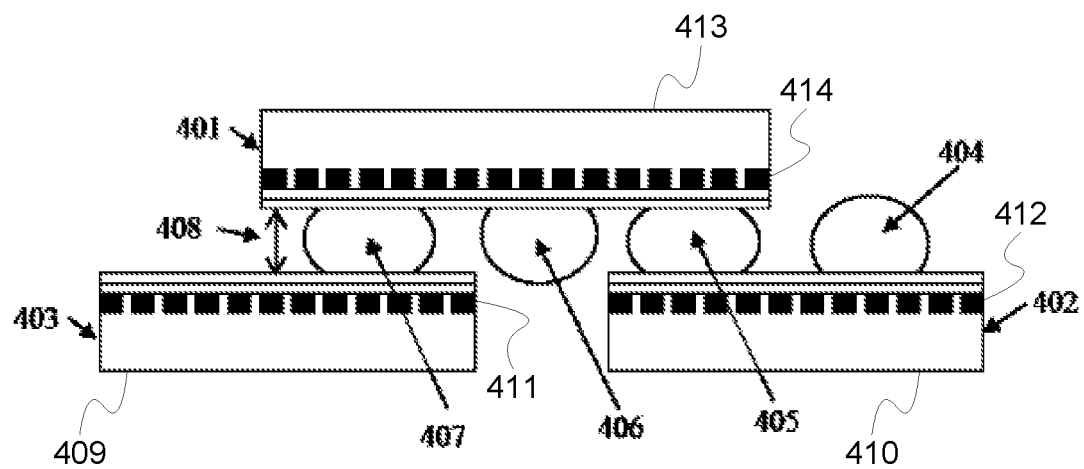
FIG. 4 is a diagram illustrating an Inter-Chip Bridge in accordance with some embodiments of the present invention.

FIG. 4 illustrates an Inter-Chip Bridge operation. To transport a droplet from one LOC system 402 to the other LOC system 403, an Inter-Chip Bridge 401 is used. The LOC system 402 and LOC system 403 are placed side by side and an Inter-Chip Bridge 401 is placed face-to-face to the two LOC systems with a gap distance 408 in between. The gap distance 408 is small enough to create a covered configuration for the droplet. A droplet in location 404 on LOC system 402 is in an open configuration. By actuating the electrodes 412 on a first plate 410 on LOC system 402 in a direction from location 404 to 405, the droplet moves from location 404 to location 405 and the droplet is now in a covered configuration. Then by actuating the electrodes 413 on a second plate 413 on Inter-Chip Bridge 401 in the direction from location 405 to location 407 on electrodes 411 on the third plate 409, the droplet moves from location 405 location 407 via location 406. Depending on the separation between the two LOC systems, the droplet is in the open configuration when passing by location 406.

Figure 5:
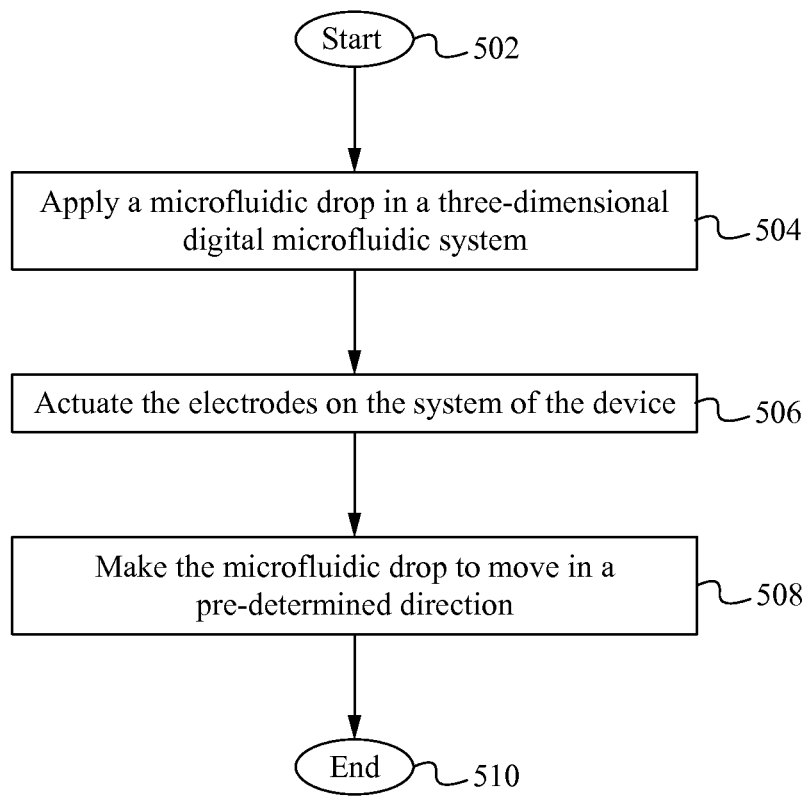
FIG. 5 is a flow chart illustrating a method 500 of using the microfluidic system in accordance with some embodiments of the present invention.

FIG. 5 is a flow chart illustrating a method 500 of using the microfluidic system in accordance with some embodiments of the present invention. The method 500 is able to start at Step 502. At Step 504, a microfluidic drop on a three-dimensional digital microfluidic system is applied. At Step 506, the electrodes on the system of the device are actuated. At Step 508, the microfluidic drop is moved in a predetermined direction. The method 500 is able to stop at Step 510.

In some embodiments, the present invention comprises two face-to-face plates that form the base of a two-layer microfluidic operation and a dual open/covered hybrid structure. In some embodiments, the inter-layer microfluidic connection is included in the three-dimensional system. In some embodiments, the present invention is superior than the typical two-dimensional system in a way that some embodiments of the present invention includes the combinations of both open and covered configuration of the two-dimensional system to provide better routing capability in one system and to provide the ability to bridge multiple microfluidic systems together. In some embodiments, the three-dimensional digital microfluidic system comprises a Dual-Layer System. In some other embodiments, the three-dimensional digital microfluidic system comprises an Inter-Chip Bridge.

In some embodiments, the three-dimensional digital microfluidic system comprises two face-to-face plates separated by a gap in between. In other embodiments, the two plates have droplet actuation electrodes on them. In some other embodiments, the electrodes on the two plates face each other. The droplets can be manipulated by a sequence of actuation of the electrodes on either or both plates to perform the desired functions. The gap is in the range of 1 μm to 10 cm. In some embodiments, an open configuration is a droplet sitting on a plate without touching the other plate. The droplets are able to be actuated by the electrodes on the plate where droplets are sitting. In some embodiments, a covered configuration is a droplet touched both plates and sandwiched between the top plate and the bottom plate. The droplets are able to be actuated by the electrodes on the top plate and/or the bottom plate. In some embodiments, the Dual-Layer System is constructed with two plates, and the two plates face each other in an angle. Because of the construction with an angle, the gap distances between the two plates are smaller on one side and bigger on the opposite side.

The angled structure creates a dual open and covered configuration. Droplets in covered configuration sandwiched between two plates near the smaller gap distance. The droplets in wider gap locations are in open configuration. Open or covered configurations are able to depend on the sizes of droplets. The back and forth motions between open and covered regions are able to be performed under electrowetting actuation. The tilted angle can be in one dimensional such that the gap differences are only along one axis (x- or y-axis) or two dimensional such that both x-axis and y-axis have different gaps.

The droplets on open region are able to move from one plate to another plate through the inter-layer connection in a Dual-Layer System. A drop originally in an open configuration on one plate is moved by actuating the electrodes on the plate where the droplet sits to the direction of narrow gap and the droplet eventually touches both plates and in a covered configuration. Then by actuating the electrodes on the other plate in the direction to the wider gap, the droplet breaks out from the covered region and results in an open configuration on the other plate.

In some embodiments, the first LOC system and the second LOC system are placed side by side with the operating surface toward the same direction. An Inter-Chip Bridge is placed between the two LOC systems and face to the two LOC systems with overlaps to both LOC systems, which form covered regions to transport the droplet to/from the Inter-Chip Bridge. A gap distance is between the Inter-Chip Bridge and the two LOC systems. The gap distance is small enough to create a covered configuration for the droplet. The first LOC system and the second LOC system is able to be either covered configuration or open configuration.

In an open configuration on the first LOC system, the droplet is eventually touches the Inter-Chip Bridge and becomes a covered configuration on the first LOC system by actuating the electrodes on LOC system in the direction toward the Inter-Chip Bridge. Then by actuating the electrodes on Inter-Chip Bridge in the direction toward the second LOC system, the droplet moves from the first LOC system to the second LOC system. When the droplet arriving the second LOC system side, it is under covered configuration. If the second LOC system operates in an open configuration then the droplet needs to move from the covered configuration into the open configuration.

In some embodiments, a method of using a three-dimensional digital microfluidic system comprising a Dual-Layer System that enables microfluidic operations on dual layers and an Inter-Chip Bridge that enables the inter-chip droplet transport capabilities. The Dual-Layer System provides better capabilities to route droplets to blocked locations or to avoid unwanted path contaminations. A LOC system can be partitioned into smaller self-contained modules and the modules are connected by the Inter-Chip Bridge. The components with incompatible manufacturing are able to be combined in a single LOC system for heterogeneous integration by the Inter-Chip Bridge. Two or more LOC systems are able to be connected by the Inter-Chip Bridge to form a bigger system.

The method is able to further comprise more than one Dual-Layer System working together as a system. The third plate or fourth plate is able to be added to one of the plates of the Dual-Layer System to form multiple-Dual-Layer Systems. The method is able to further comprise more than one Inter-Chip Bridge working together as a system. The second or third Inter-Chip Bridges is able to be added to the system to form multiple-Inter-Chip-Bridge systems. The method further comprises the hybrid system, which is a combined Dual-Layer System and Inter-Chip Bridge system. The microfluidic operations of the dual-layer system leverage the best of a dual open/covered hybrid design that droplet transporting and mixing are performed on the open region of the stacked dual-layer system and droplet creation and splitting are performed at the covered region.

In operation, the three-dimensional digital microfluidic system is able to transport microfluidic drops/fluids using electrical attractions. By actuating the electrodes in sequence, the microfluidic drops are able to be moved by a pulling/attracting force generated by the electrodes.

The present invention is able to be utilized in pharmaceutical industry for making drug transporting systems.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A three-dimensional digital microfluidic system comprising:
   a. a first plate with a first electrode, wherein the first plate is a first Lab-on-Chip system;
   b. a second plate with a second electrode, wherein the second electrode comprises an inter-chip bridge;
   c. a third plate with a third electrode, wherein the third plate is on a second Lab-on-Chip system; wherein the inter-chip bridge serves as an intermediate structure configured to transport a microfluidic drop in an open configuration between a covered configuration of the first Lab-on-Chip system and a covered configuration of the second Lab-on-Chip system.

2. The system of claim 1, wherein the first plate is parallel to the second plate.

3. The system of claim 1, wherein the first electrode is facing the second electrode.

4. The system of claim 1 further comprises a gap between the first plate and the second plate.

5. The system of claim 4, wherein the gap is in the range of 1 μm to 10 cm.

6. The system of claim 1, wherein each of the first electrode and the second electrode comprises at least one droplet actuating electrode.

7. The system of claim 1, wherein the microfluidic droplet is manipulated by actuating in sequence of the electrodes on either or both plates.

8. The system of claim 1, wherein the microfluidic droplet is in physical contact with either one of the first plate and the second plate.

9. The system of claim 1, wherein the microfluidic droplet is in physical contact with both of the first and the second plate.

10. The system of claim 1, wherein the microfluidic droplet is actuated by the electrodes on the first plate, the second plate, or a combination thereof.

11. The system of claim 1, further comprising an electrowetting actuation mechanism to control a motion of the microfluidic droplet.

12. The system of claim 1 further comprises a controlling unit controlling a movement of the microfluidic droplet, such the microfluidic droplet is able to be moved to be in a physical contact with either one of the first plate or the second plate or both.

13. A three-dimensional digital microfluidic system comprising:
   a. a first plate with a first electrode, wherein the first plate is on a first Lab-on-Chip system;
   b. a second plate with a second electrode, wherein the second plate is on a second Lab-on-Chip system; and
   c. a bridge plate with third electrodes facing the first electrode and the second electrode, wherein the bridge plate comprises at least a first portion overlapping with the first plate and at least a second portion overlapping with the second plate and a third portion in an open configuration between the first plate and the second plate.

14. The system of claim 13 further comprises a microfluidic droplet.

15. The system of claim 14, wherein the microfluidic droplet is sandwiched between the first plate and the bridge plate.

16. The system of claim 14, wherein the microfluidic droplet is sandwiched between the second plate and the bridge plate.

17. The system of claim 14, wherein the microfluidic droplet is only in physical contact with the bridge plate.

18. The system of claim 14 further comprises a first gap between the first plate and the bridge plate and a second gap between the bridge plate and the second plate.

19. The system of claim 18, wherein the first gap is equal in size to the size of the second gap.

20. A method of using a three-dimensional digital microfluidic system comprising moving a microfluidic drop from a first plate of a first Lab-on-Chip system to a second plate of a second Lab-on-Chip system via a bridge plate, wherein the first plate, the second plate, and the bridge plate comprise a first electrode, a second electrode, and a bridge electrode, respectively, and wherein a first portion of the bridge plate overlaps the first plate, a second portion of the bridge plate overlaps the second plate, and a third portion of the bridge plate between the first and second plates is in an open configuration.

21. The method of claim 20 further comprising actuating the first electrode, the bridge electrode, and the second electrode in sequence such that the microfluidic drop is transported from the first plate to the second plate.

22. The method of claim 20, wherein the first electrode and the second electrode are facing the bridge electrode.

* * * * *